(12) United States Patent
Holtz et al.

(10) Patent No.: US 9,765,980 B2
(45) Date of Patent: Sep. 19, 2017

(54) MODULAR, SELF-CONTAINED, MOBILE CLEAN ROOM

(71) Applicant: G-CON MANUFACTURING, INC., College Station, TX (US)

(72) Inventors: R. Barry Holtz, Houston, TX (US); Troy Arledge, Rockdale, TX (US); Philip B. Maples, Pilot Point, TX (US); David M. Shanahan, Dallas, TX (US)

(73) Assignee: G-CON MANUFACTURING, INC., College Station, TX (US)

( * ) Notice: Subject to any disclaimer, the term of this patent is extended or adjusted under 35 U.S.C. 154(b) by 0 days.

(21) Appl. No.: 14/858,857

(22) Filed: Sep. 18, 2015

(65) Prior Publication Data

US 2016/0010884 A1    Jan. 14, 2016

Related U.S. Application Data (63) Continuation of application No. 12/856,888, filed on Aug. 16, 2010.
(Continued)

(51) Int. Cl.
*F24F 3/16* (2006.01)
*B01L 1/04* (2006.01)
*C12M 1/12* (2006.01)

(52) U.S. Cl.
CPC ...... *F24F 3/16* (2013.01); *B01L 1/04* (2013.01); *C12M 37/00* (2013.01); *F24F 3/161* (2013.01); *Y10T 29/49826* (2015.01)

(58) Field of Classification Search
CPC ..................................................... F24F 3/161
See application file for complete search history.

(56) References Cited

U.S. PATENT DOCUMENTS

| 1,967,511 A | 7/1934 | Meyer |
| 1,991,536 A | 2/1935 | Austin |

(Continued)

FOREIGN PATENT DOCUMENTS

| CN | 2012/81413 Y | 7/2009 |
| DE | 8913876 U1 | 1/1990 |

(Continued)

OTHER PUBLICATIONS

"Fast-track clean room building," European Semiconductor, UK, Mar. 1992, vol. 14, No. 3, pp. 43, 45.
(Continued)

*Primary Examiner* — Alissa Tompkins
*Assistant Examiner* — Phillip E Decker
(74) *Attorney, Agent, or Firm* — Kilpatrick Townsend & Stockton LLP (57) ABSTRACT

Biosafety units, methods of making, and sealing the same are disclosed herein. The units comprise at least one controlled air, sealable, sterilizable cleanroom; and a mechanical system room adjacent to the cleanroom comprising: at least two air handling units in a support room adjacent the cleanroom that provide redundant air to the cleanroom with at least Class 100,000 air purity, the air handling units connected to a one or more supply ducts to the cleanroom, and an exhaust duct in communication with the cleanroom and the air handling unit exhaust, wherein a pressure gradient is formed between the cleanroom and the exterior of the structure; and at least two power supplies that provide redundant power to electrical outlets in the cleanroom, wherein the at least two power supplies are connectable to one or more external power sources and the structure is pre-validatable or validated for pharmaceutical manufacturing.

20 Claims, 7 Drawing Sheets

Related U.S. Application Data (60) Provisional application No. 61/234,302, filed on Aug. 16, 2009.

(56) References Cited

U.S. PATENT DOCUMENTS

| | | | |
|---|---|---|---|
| 2,156,859 A | 5/1939 | Lowe | |
| 2,168,725 A | 8/1939 | Whelan | |
| 3,115,819 A | 12/1963 | Mahlmeister | |
| 3,378,963 A | 4/1968 | Obata | |
| 3,456,829 A | 7/1969 | Glassmeyer | |
| 3,470,871 A | 10/1969 | Shoen | |
| 3,623,283 A | 11/1971 | Abromavage et al. | |
| 3,638,641 A | 2/1972 | Abromavage et al. | |
| 3,678,639 A * | 7/1972 | Panitz | E04B 1/34336 |
| | | | 52/169.2 |
| 3,742,932 A | 7/1973 | Greenspan | |
| 3,756,342 A | 9/1973 | Burdick | |
| 3,766,844 A | 10/1973 | Donnelly | |
| 4,255,912 A | 3/1981 | Kovacs | |
| 4,267,769 A | 5/1981 | Davis et al. | |
| 4,304,224 A | 12/1981 | Fortney | |
| 4,327,529 A | 5/1982 | Bigelow et al. | |
| 4,409,889 A | 10/1983 | Burleson | |
| 4,549,472 A | 10/1985 | Endo et al. | |
| 4,554,766 A | 11/1985 | Ziemer et al. | |
| 4,599,829 A | 7/1986 | DiMartino, Sr. | |
| 4,667,579 A | 5/1987 | Daw | |
| 4,667,580 A | 5/1987 | Wetzel | |
| 4,682,418 A | 7/1987 | Tuss et al. | |
| 4,693,175 A | 9/1987 | Hashimoto | |
| 4,694,736 A | 9/1987 | Yamagata | |
| 4,731,961 A | 3/1988 | Bona | |
| 4,820,931 A | 4/1989 | Dunbar | |
| 4,850,268 A | 7/1989 | Saito et al. | |
| 4,869,156 A | 9/1989 | Hutton | |
| 4,883,512 A | 11/1989 | Griffis | |
| 4,923,352 A | 5/1990 | Tamura et al. | |
| 5,029,518 A | 7/1991 | Austin | |
| 5,058,491 A | 10/1991 | Wiemer et al. | |
| 5,096,477 A | 3/1992 | Shinoda et al. | |
| 5,125,203 A | 6/1992 | Daw | |
| 5,128,855 A | 7/1992 | Hilber | |
| 5,152,814 A | 10/1992 | Nelson | |
| 5,163,517 A | 11/1992 | Kozai et al. | |
| 5,195,922 A | 3/1993 | Genco | |
| 5,279,632 A | 1/1994 | Decker et al. | |
| 5,326,316 A | 7/1994 | Hashimoto et al. | |
| 5,344,365 A | 9/1994 | Scott et al. | |
| 5,350,336 A | 9/1994 | Chen et al. | |
| 5,474,411 A | 12/1995 | Schoenfeld et al. | |
| 5,511,594 A | 4/1996 | Brennan et al. | |
| 5,562,539 A | 10/1996 | Hashimoto et al. | |
| 5,626,786 A | 5/1997 | Huntington et al. | |
| 5,641,354 A | 6/1997 | Sakauchi | |
| 5,656,491 A | 8/1997 | Cassani et al. | |
| 5,706,846 A | 1/1998 | Sutton | |
| 5,713,791 A | 2/1998 | Long et al. | |
| 5,752,985 A | 5/1998 | Nagafune et al. | |
| 5,795,356 A | 8/1998 | Leveen | |
| 5,941,846 A | 8/1999 | Duffy et al. | |
| 6,044,596 A | 4/2000 | Driggett | |
| 6,132,309 A * | 10/2000 | Panelli | F24F 3/161 |
| | | | 454/187 |
| 6,179,358 B1 * | 1/2001 | Hirayama | E04H 3/08 |
| | | | 296/24.38 |
| 6,196,514 B1 | 3/2001 | Kienholz | |
| 6,304,005 B1 | 10/2001 | Aoki et al. | |
| 6,360,494 B1 | 3/2002 | Emerson | |
| 6,394,523 B1 | 5/2002 | Yoo et al. | |
| 6,397,755 B1 | 6/2002 | Kamler | |
| 6,450,411 B1 | 9/2002 | Rash et al. | |
| 6,512,384 B1 | 1/2003 | Lagowski et al. | |
| 6,602,128 B1 | 8/2003 | Spengler | |
| 6,634,149 B2 | 10/2003 | Cates et al. | |
| 6,688,055 B2 | 2/2004 | Lindsley | |
| 6,869,457 B2 | 3/2005 | Nakagawa | |
| 6,925,761 B1 * | 8/2005 | De La Marche | E04B 1/34815 |
| | | | 52/220.1 |
| 6,960,236 B1 | 11/2005 | Tamura | |
| 6,969,102 B2 | 11/2005 | Orischak et al. | |
| 7,022,009 B2 | 4/2006 | Kim | |
| 7,160,717 B2 | 1/2007 | Everett | |
| 7,162,833 B2 | 1/2007 | Faris | |
| 7,222,246 B2 | 5/2007 | Pomaranski et al. | |
| 7,272,733 B2 | 9/2007 | Pomaranski et al. | |
| 7,323,025 B2 | 1/2008 | Weidner | |
| 7,326,355 B2 * | 2/2008 | Graetz | A61M 1/0236 |
| | | | 141/10 |
| 7,472,513 B2 | 1/2009 | Bula | |
| 7,511,960 B2 | 3/2009 | Hillis et al. | |
| 7,527,664 B2 | 5/2009 | Jackson | |
| 7,586,420 B2 | 9/2009 | Fischer et al. | |
| 7,724,513 B2 | 5/2010 | Coglitore et al. | |
| 7,827,738 B2 | 11/2010 | Abrams et al. | |
| 7,861,102 B1 | 12/2010 | Ranganathan et al. | |
| 7,934,124 B2 | 4/2011 | Bechtolsheim et al. | |
| 7,985,382 B1 | 7/2011 | Henry et al. | |
| 8,061,080 B2 | 11/2011 | Loebl et al. | |
| 8,065,560 B1 | 11/2011 | Patil | |
| 8,147,301 B2 | 4/2012 | Ghattas | |
| 8,239,340 B2 | 8/2012 | Hanson | |
| 8,322,086 B2 | 12/2012 | Weber | |
| 8,371,912 B2 | 2/2013 | Ozeki | |
| 8,479,038 B1 | 7/2013 | Patil | |
| 8,584,349 B2 | 11/2013 | Scanlon et al. | |
| 9,187,894 B2 | 11/2015 | Zadok et al. | |
| 9,518,748 B2 * | 12/2016 | Holtz | C12M 37/00 |
| 9,671,798 B2 | 6/2017 | Hodge et al. | |
| 2002/0174888 A1 | 11/2002 | Brown | |
| 2003/0045226 A1 | 3/2003 | Yokoyama et al. | |
| 2003/0140555 A1 | 7/2003 | Saether | |
| 2004/0194484 A1 | 10/2004 | Zou | |
| 2005/0082445 A1 | 4/2005 | Groves | |
| 2005/0091916 A1 | 5/2005 | Faris | |
| 2005/0124010 A1 | 6/2005 | Short et al. | |
| 2005/0154494 A1 | 7/2005 | Ahmed | |
| 2005/0193643 A1 | 9/2005 | Pettus | |
| 2006/0107635 A1 | 5/2006 | Homan et al. | |
| 2006/0217056 A1 | 9/2006 | Gomi et al. | |
| 2006/0234621 A1 | 10/2006 | Desrochers | |
| 2007/0039260 A1 | 2/2007 | Haddad | |
| 2007/0089854 A1 | 4/2007 | Jaisinghani | |
| 2007/0130844 A1 | 6/2007 | Arts et al. | |
| 2007/0132262 A1 | 6/2007 | Chui Peng Sun et al. | |
| 2007/0167126 A1 | 7/2007 | Ghattas | |
| 2007/0228692 A1 | 10/2007 | Kern et al. | |
| 2007/0251145 A1 | 11/2007 | Bursatore | |
| 2007/0253831 A1 | 11/2007 | Lee | |
| 2008/0005976 A1 * | 1/2008 | Montaigne | E04H 9/14 |
| | | | 52/79.1 |
| 2008/0047207 A1 | 2/2008 | Lam | |
| 2008/0047224 A1 | 2/2008 | Lam | |
| 2008/0086980 A1 | 4/2008 | Martin | |
| 2008/0201008 A1 | 8/2008 | Twelves et al. | |
| 2008/0302004 A1 | 12/2008 | Lin | |
| 2009/0122533 A1 | 5/2009 | Brukilacchio | |
| 2009/0126285 A1 | 5/2009 | Suh | |
| 2009/0199470 A1 | 8/2009 | Capen | |
| 2009/0305626 A1 | 12/2009 | Hope | |
| 2010/0031564 A1 | 2/2010 | Loebl et al. | |
| 2010/0112677 A1 | 5/2010 | Onishi et al. | |
| 2010/0112926 A1 | 5/2010 | Ozeki | |
| 2010/0192493 A1 | 8/2010 | Nakai | |
| 2010/0304658 A1 | 12/2010 | Grcevic | |
| 2011/0053486 A1 | 3/2011 | Holtz et al. | |
| 2011/0217917 A1 | 9/2011 | Sulva | |
| 2011/0219953 A1 | 9/2011 | Schreiber | |
| 2011/0258837 A1 | 10/2011 | Scannon et al. | |
| 2012/0077429 A1 * | 3/2012 | Wernimont | F24F 3/161 |
| | | | 454/187 |
| 2012/0099035 A1 | 4/2012 | Burgess | |
| 2012/0181869 A1 | 7/2012 | Chapel et al. | |
| 2013/0109291 A1 | 5/2013 | Holtz et al. | |

(56) References Cited

U.S. PATENT DOCUMENTS

| | | |
|---|---|---|
| 2014/0179216 A1 | 6/2014 | Walters |
| 2015/0101264 A1 | 4/2015 | Jornitz |
| 2015/0159127 A1 | 6/2015 | Guerini et al. |
| 2016/0010883 A1 | 1/2016 | Jornitz et al. |

FOREIGN PATENT DOCUMENTS

| | | |
|---|---|---|
| DE | 4007740 A1 | 9/1991 |
| EP | 940292 A2 | 9/1999 |
| EP | 2098111 | 9/2009 |
| JP | 61-101733 | 5/1986 |
| JP | 2206526 A | 8/1990 |
| JP | H06174279 A | 6/1994 |
| JP | 06-183511 | 7/1994 |
| JP | 10-077711 | 3/1998 |
| JP | 11166269 A | 6/1999 |
| JP | 2000/54654 A | 2/2000 |
| JP | 2000/142211 A | 5/2000 |
| JP | 2001/141274 A | 5/2001 |
| JP | 2002-221464 | 8/2002 |
| JP | 2004-033498 | 5/2004 |
| JP | 2004-233021 | 8/2004 |
| JP | 2007-107779 | 4/2007 |
| JP | 2007-107830 | 4/2007 |
| JP | 2008/304989 A | 12/2008 |
| JP | 2009/002634 A | 1/2009 |
| KR | 100675682 | 12/2006 |
| KR | 20060130383 A | 12/2006 |
| TW | 2009/12219 A | 3/2009 |
| WO | 00/02618 A1 | 1/2000 |
| WO | 2004/005170 A1 | 1/2004 |
| WO | 03/095765 A2 | 6/2007 |
| WO | 2007/067656 | 6/2007 |
| WO | 2008/018671 A1 | 2/2008 |
| WO | 2013/132086 A1 | 12/2013 |

OTHER PUBLICATIONS

Anonymous, "Clean-room products and equipment," Medical Device Technology, Chester, Jan./Feb. 2005, vol. 16, pp. 43-44. Document URL: http://search.proquest.com/docview/195254246?accountid=142944.

Oliviera, Tony, :Factory in a Clean Room, Quality Progress, Milwaukee, Jan. 1990, vol. 23, No. 1, p. 37. Document URL: http://search.proquest.com/docview/214764942?accountid=142944.

Watkins, B., "Clean rooms: their performance and design," Journal of Semi-Custom ICs, UK, Mar. 1985, vol. 2, No. 3, pp. 36-40.

Astra-Zeneca Pharmaceutical Building, "Vanguard Modular Building Systems Brochure," Dec. 9, 2004, 2 pages.

Pharmadule Press Release "Pharmadule Doubles Production Capacity and Acquires Patent for Modular Biotech Plants," Sep. 27, 2002, 1 page, http://www.pharmadule.com/pharmadule-doubles-production-capacity.

Muth, Laboratory Design, "Moudlar Construction: Pros and Cons for the Lab Building," R&D Magazine, Jun. 17, 2009, 5 pages.

Hovair Systems, Pneumatic Powered Load Moving Systems—Air Bering Principle, https://webarchive.org/web/20080521025052/http://www.hovair.com/air-bearing-info/features-and-benefits.htm, May 21, 2008.

* cited by examiner

MODULAR, SELF-CONTAINED, MOBILE CLEAN ROOM

CROSS-REFERENCES TO RELATED APPLICATIONS

This application is a continuation of U.S. application Ser. No. 12/856,888, filed Aug. 16, 2010, which claims the benefit of U.S. Provisional Application No. 61/234,302, filed Aug. 16, 2009, the contents of which are hereby incorporated by reference in their entireties for all purposes.

STATEMENT AS TO RIGHTS TO INVENTIONS MADE UNDER FEDERALLY SPONSORED RESEARCH AND DEVELOPMENT

Not Applicable

TECHNICAL FIELD

Embodiments of the present invention relate in general to the field of biosafety units, and more particularly, to modular, self-contained, mobile rooms for medical treatments or the manufacture of medical products requiring clean rooms.

BACKGROUND

Without limiting the scope of the invention, its background is described in connection with mobile modular plants.

U.S. Pat. No. 5,656,491, issued to Cassani, et al., teaches a mobile-module plant for the development and the production of biotechnological products on a pilot scale. Briefly, the patent teaches a mobile-module plant for the development and the production of biotechnological products on a pilot scale comprising equipments for the production, separation, purification and finishing of said products and auxiliary equipments, wherein the plant consists of at least two mobile modules suitable for being connected together and integrated one with the other. Each of the mobile modules comprises a movable container. At least one of the movable containers is provided with a preselected own set of said equipments. At least one of the movable containers is aseptic.

BRIEF SUMMARY

In one embodiment, the present is an unitary structure comprising: at least one controlled air, sealable, sterilizable cleanroom; and a mechanical system room adjacent to the cleanroom comprising: at least two air handling units in a support room adjacent the cleanroom that provide redundant air to the cleanroom with at least Class 100,000 air purity, the air handling units connected to one or more supply ducts to the cleanroom, and an exhaust duct in communication with the cleanroom and the air handling unit exhaust, wherein a pressure gradient is formed between the cleanroom and the exterior of the structure; and at least two power busses that provide power to electrical outlets 77 (see FIG. 3) in the cleanroom from two sources, wherein the at least two power supplies are connectable to one or more external electrical power sources and the structure is pre-validatable or prevalidated for pharmaceutical manufacturing. In one aspect, the structure further comprises a unitary, redundant information technology system that connects to an intranet, an extranet or both, wherein the system connects to and controls one or more sensors. In another aspect, the structure further comprises one or more external controls connected to one or more sensors that monitor, temperature, humidity, air pressure, equipment status, security, chemical or biological contamination, hard wired internet or wireless connections. In another aspect, the structure further comprises universal connectors including at least one of an electrical, water, wastewater, gas, HVAC, water or air filtration inputs/outputs.

In another aspect of the structure of the invention the equipment is fixed to the structure prior to validation. In another aspect, the air handling unit and power busses have instantaneous fail-over during operation of the cleanroom without loss of air or power to the cleanroom. In another aspect, the structure comprises additional fail-over systems to provide service to the cleanroom selected from at least one of the water, gas, drain water, chilled water or wastewater systems. In another aspect, the structure comprises water, gas, drain water, or wastewater systems and these systems are repairable in the mechanical system room without loss of service to the cleanroom. In another aspect, the redundant systems that support the clean room can be swapped without specialized electrical, water, waste-water personnel or permits. In another aspect, the structure can be moved without disconnecting from the electrical, water, drain water, waste-water, gas, chilled water or hot water supplies connected to the structure. In another aspect, the structure comprises at least one or reinforced floors, I-beams below the floor, vibration dampeners or footings. In another aspect, the structure further comprises a first and a second passage into the cleanroom for ingress and egress from the sealable cleanroom. In another aspect, the structure is aluminum. In another aspect, the mechanical system room may be serviced without entering the cleanroom. In another aspect, the one or more supply ducts comprises one or more baffles adapted to vary the internal pressure in one or more areas within the cleanroom thereby creating a pressure gradient between the internal pressure and atmospheric pressure external to the structure. In another aspect, the internal pressure can be varied to be greater than, less than or equal to the atmospheric pressure. In another aspect, the air flow within the cleanroom is laminar. In another aspect, the cleanroom is provided with at least Class 10,000, 1,000, 100, or 10 air purity. In another aspect, the cleanroom comprises at least one pre-validatable or prevalidated, work table, work surface, sink, cabinet, centrifuge, tissue culture hood, chemical handling unit, stirrer tank, chromatography column, cell sorter, bioreactor, refrigerator, freezer, incubator, biosafety cabinet, temperature cycler, vacuum, or freeze drier, culture media, water, solvents, disposables, pipettes, disposable containers, surveillance equipment, bags, office items or chairs. In another aspect, at least a portion of the structure is thermally insulated.

In yet another aspect, the structure further comprises one or more sealable passages for pipes, electrical wiring, pneumatic or hydraulic lines, gas lines, communications wiring, and wireless connectivity. In another aspect, the cleanroom further comprises one or more sealable conduits to transfer materials to and from the cleanroom. In another aspect, the structure further comprises sufficient air-bearings under the structure to permit movement of the structure. In another aspect, the structure is adapted for transport via land, sea or air. In another aspect, the structure further comprises one or more of an air conditioner; a water cooling unit; a steam boiler; a water softener; a reverse osmosis unit; a still; a heat exchanger; a hot water production system; and an air compressor. In another aspect, the structure further comprises a sealed envelope following validation for cGMP manufacturing. In another aspect, the structure is portable.

In another embodiment, the present invention is a rapid deployment patient care facility comprising: at least one controlled air, sealable, sterilizable cleanroom; at least two air handling units in a support room adjacent the cleanroom that provide redundant air to the cleanroom with at least Class 100,000 air purity, the air handling units connected to a one or more supply ducts to the cleanroom, and an exhaust duct in communication with the cleanroom and the air handling unit exhaust, wherein a pressure gradient is formed between the cleanroom and the exterior of the structure; and at least two power supplies that provide redundant power to electrical outlets in the cleanroom, wherein the at least two power supplies are connectable to one or more external power sources and the structure is validatable for patient care. In one aspect, the facility is collapsible. In another aspect, the cleanroom comprises at least one pre-validatable, work table, work surface, sink, cabinet, centrifuge, tissue culture hood, chemical handling unit, stirrer tank, chromatography column, cell sorter, bioreactor, refrigerator, freezer, incubator, biosafety cabinet, temperature cycler, vacuum, or freeze drier, culture media, water, solvents, disposables, pipettes, disposable containers, surveillance equipment, bags, office items or chairs. In another aspect, at least a portion of the structure is thermally insulated. In another aspect the facility further comprises one or more sealable passages for pipes, electrical wirings, pneumatic or hydraulic lines, gas lines, communications wiring, and wireless connectivity and one or more sealable conduits to transfer materials to and from the facility. In another aspect the facility comprises sufficient air-bearings under the facility to permit movement of the facility. In yet another aspect the facility further comprises one or more of an air conditioner; a water cooling unit; a steam boiler; a water softener; a reverse osmosis unit; a still; a heat exchanger; a hot water production system; and an air compressor. In another aspect the facility is adapted for transport via land, sea or air. In another aspect the facility further comprises a sealed envelope following validation for cGMP manufacturing.

In yet another embodiment, the present invention is a biosafety unit comprising: at least one controlled air, sealable, sterilizable cleanroom; and a mechanical system room adjacent to the cleanroom comprising two or more redundant systems, the redundant systems comprising: at least two air handling units in a support room adjacent the cleanroom that provide redundant air to the cleanroom with at least Class 100,000 air purity, the air handling units connected to a one or more supply ducts to the cleanroom, and an exhaust duct in communication with the cleanroom and the air handling unit exhaust, wherein a pressure gradient is formed between the cleanroom and the exterior of the unit; and at least two power supplies that provide redundant power to electrical outlets in the cleanroom, wherein the at least two power supplies are connectable to one or more external power sources and the unit is pre-validatable or validated for pharmaceutical manufacturing. In another aspect, the unit is validated by an applicable regulatory agency. In another aspect, the unit is validated and further comprises a sealed envelope following validation for cGMP manufacturing. In another aspect, the unit further comprises a unitary, redundant information technology system that connects to an intranet, an extranet or both, wherein the system connects to and controls one or more sensors.

In another aspect, the unit further comprises one or more external controls connected to one or more sensor that monitor, temperature, humidity, air pressure, equipment status, security, chemical or biological contamination, hard wired internet connection or wireless connection. In another aspect, the unit further comprises universal connectors including at least one or an electrical, water, wastewater, gas, HVAC, water or air filtration inputs/outputs. In another aspect, the equipment is fixed to the unit prior to validation. In another aspect, the air handling unit and power busses have instantaneous fail-over during operation of the cleanroom without loss of air or power to the cleanroom. In another aspect, the unit comprises additional fail-over systems to provide service to the cleanroom selected from at least one of the water, gas, drain water, chilled water or wastewater systems. In another aspect, the unit comprises water, gas, drain water, or wastewater systems and these systems are repairable in the mechanical system room without loss of service to the cleanroom. In another aspect, the redundant systems that support the clean room can be swapped without specialized electrical, water, waste-water personnel or permits. In another aspect, the unit can be moved without disconnecting from the electrical, water, drain water, waste-water, gas, chilled water or hot water supplies connected to the unit. In another aspect, the unit further comprises a first and a second passage into the cleanroom for ingress and egress from the sealable cleanroom. In another aspect, the mechanical system room may be serviced without entering the cleanroom. In another aspect, the cleanroom is provided with at least Class 10,000, 1,000, 100, or 10 air purity. In another aspect, the cleanroom comprises at least one pre-validatable or prevalidated, centrifuge, tissue culture hood, chemical handling unit, stirrer tank, chromatography column, cell sorter, bioreactor, refrigerator, freezer, incubator, biosafety cabinet, temperature cycler, vacuum, or freeze drier, culture media, water, solvents, disposables, pipettes, disposable containers. In another aspect the cleanroom comprises a work table, work surface, sink, cabinet surveillance equipment, bags, office items or chairs. In another aspect, the unit further comprises one or more sealable passages for pipes, electrical wiring, pneumatic or hydraulic lines, gas lines, communications wiring, and wireless connectivity. In another aspect, the unit includes sufficient air-bearings under the unit to permit movement of the unit. In another aspect, the unit is adapted for transport via land, sea or air. In another aspect, the unit further comprises one or more of an air conditioner; a water cooling unit; a steam boiler; a water softener; a reverse osmosis unit; a still; a heat exchanger; a hot water production system; and an air compressor. In another aspect, the unit further comprises a sealed envelope following validation for cGMP manufacturing. In another aspect, the unit is portable.

Yet another aspect of the present invention includes a method of making a unitary pre-validatable or prevalidated unit comprising: building at least one controlled air, sealable, sterilizable cleanroom; and connecting to the building a mechanical system room adjacent to the cleanroom comprising: at least two air handling units in a support room adjacent the cleanroom that provide redundant air to the cleanroom with at least Class 100,000 air purity, the air handling units connected to a one or more supply ducts to the cleanroom, and an exhaust duct in communication with the cleanroom and the air handling unit exhaust, wherein a pressure gradient is formed between the cleanroom and the exterior of the unit; and at least two power busses that provide power to electrical outlets in the cleanroom from two sources, wherein the at least two power supplies are connectable to one or more external electrical power sources and the unit is pre-validatable or prevalidated for pharmaceutical manufacturing. In one aspect, the method further comprises the step of validating the unit by an applicable regulatory agency. In one aspect, the method further comprises the step of validating the unit and surrounding the unit with a sealed envelope following validation for cGMP manufacturing. In one aspect, the method further comprises the step of connecting a unitary, redundant information technology system that connects to an intranet, an extranet or both, wherein the system connects to and controls one or more sensors. In one aspect, the method further comprises the step of connecting one or more external controls connected to one or more sensor that monitor, temperature, humidity, air pressure, equipment status, security, chemical or biological contamination, hard wired internet connection or wireless connection to the unit. In one aspect, the method further comprises the step of selecting universal connectors including at least one or an electrical, water, wastewater, gas, HVAC, water or air filtration inputs/outputs to standardize the unit. In one aspect, the method further comprises the step of fixing equipment in the cleanroom prior to validation.

In one aspect, the method further comprises the step of adapting the air handling unit and power busses to have instantaneous fail-over during operation of the cleanroom without loss of air or power to the cleanroom. In one aspect, the method further comprises the step of adding one or more fail-over systems to provide service to the cleanroom selected from at least one of the water, gas, drain water, chilled water or wastewater systems. In one aspect, the method further comprises the step of locating the water, gas, drain water, or wastewater systems, and these systems are repairable in the mechanical system room and the repairs occur without loss of service to the cleanroom. In one aspect, the method further comprises the step of connecting the redundant systems that support the clean room to be swapped without specialized electrical, water, waste-water personnel or permits. In one aspect, the method further comprises the step of connecting flexible connector 80 (see FIG. 4) that allows the unit to be moved without disconnecting from the electrical, water, drain water, waste-water, gas, chilled water or hot water supplies connected to the unit. In one aspect, the method further comprises the step of connecting to the cleanroom a first and a second passage into the cleanroom for ingress and egress to the cleanroom. In one aspect, the method further comprises the step of servicing the mechanical system room without entering the cleanroom. In one aspect, the method further comprises the step of providing the cleanroom with at least Class 10,000, 1,000, 100, or 10 air purity that can be serviced without entering the cleanroom. In one aspect, the method further comprises the step of including within the cleanroom at least one pre-validatable or prevalidated, work table, work surface, sink, cabinet, centrifuge, tissue culture hood, chemical handling unit, stirrer tank, chromatography column, cell sorter, bioreactor, refrigerator, freezer, incubator, biosafety cabinet, temperature cycler, vacuum, or freeze drier, culture media, water, solvents, disposables, pipettes, disposable containers, surveillance equipment, bags, office items or chairs. In certain embodiments, specific units comprising specific equipment can be built, loaded with equipment and prevalidated for use as an incubator room, bioreactor room, purification room, processing room, packaging room, materials' handling room, inventory room, storage room or other rooms commonly used in the treatment of patients or the manufacture or packaging of drugs or other chemicals, e.g., biologicals (e.g., proteins, vaccines, dietary supplements, drugs (e.g., those requiring regulatory approval), hybrid compositions or agents (e.g., mineral-biological composites) and small molecules (e.g., active agents and excipients for the treatment of diseases and other medical conditions). In one aspect, the method further comprises the step of connecting one or more sealable passages for pipes, electrical wiring, pneumatic or hydraulic lines, gas lines, communications wiring, and wireless connectivity to the unit. In one aspect, the method further comprises the step of positioning sufficient air-bearings under the unit to permit movement of the unit. In one aspect, the method further comprises the step of adapting the unit for transport via land, sea or air.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes a modular pharmaceutical facility for the production of, e.g., vaccines and includes all the necessary quality control, quality assurance, and lot release functions. The end product can be made within the same or an adjacent module vaccine filled in bulk vials, suitable for distribution, and compliant with all FDA current Good Manufacturing Practices (cGMP) guidelines. The following terms are used interchangeably "modular unit", "structure", "unit" or "module" to describe a unitary structure that includes at least one portion that is a sealable, working area or cleanroom in which one or more functions or processes are conducted that require a controlled working environment and a mechanical service room or area (which may be closed or open) and that support the clean room and provides redundant services to the cleanroom, e.g., air-handling, electrical, water, waste water, waste disposal, chiller and/or heated water, gas, control units and sensors, and security. These services will generally be connected to a source of the service that uses universal connectors 80 and 81 (see FIG. 4), which are those commonly used as fittings in industry (e.g., 110 or 220 volt connections, ½-1 inch liquid or gas connections, wired or wireless connections to an intra, extra or internet and the like).

As used herein the terms "validation" and "pre-validation" are intended to encompass all documented processes or acts undertaken to demonstrate that a procedure, a process or an activity will consistently yield an expected result or outcome. Validation often includes qualification of equipments and systems. Validation is a key required component of Good Manufacturing Practices (GMP) and other regulatory requirements. For example, in the pharmaceutical industry validation of a facility and the process is done prior to obtaining a regulatory approval for the commercial manufacture and sale of the pharmaceutical product. Validation activities in the pharmaceutical industry may also include trial runs (pre-validation) before performing the actual validation to set validation limits, critical manufacturing controls, alert limits, etc and to assess the potential outcome of the actual validation run. Validations routinely performed in the cleaning Validations, process validation, analytical method validation, computer System Validation, qualifying systems and equipment including: design qualification (DQ), component qualification (CQ), installation qualification (IQ), operational qualification (OQ), and process qualification (PQ).

The skilled artisan will recognize that though the structures, facilities or units described in the instant invention are validatable they may not be validated or required to be validated for certain uses and applications, particularly for non-human use or manufacture of products for non-human consumption (for e.g. veterinary applications, agriculture applications, pesticide manufacture, etc.)

Each modular unit, whether operating alone, in a suit or as part of multiple-modular unit facility, can include specific enclosed spaces for the manufacture, fermentation, growth (e.g., in a bioreactor) of the composition requiring an FDA approved, GMP or cGMP facility that includes, e.g., lights, controlled GMP areas consistent with USDA, CDC, FDA or regulations for foreign equivalents, including clean room conditions, purification, chromatography, bulk or individual vial filling, that can be arranged within, e.g., a standard factory or facility with a clearance sufficiently high to accommodate the units within. In one example, the modular units can be placed within a building shell that includes standard electrical connections, water, wastewater, air handling to which the units are connected. The present invention requires no pre-assembly or re-assembly of the multiple units as each can function independently and can be used for multiple purposes.

For example, a complete manufacturing facility can be built, within hours to days, from pre-assembled, pre-approved modular units that include all the equipment necessary for the desired function(s) for that unit within a manufacturing plant. These flexible-by-design GMP modular units allow for the design of production facilities for the rapid deployment and redeployment of units based on the design needs. For example, one modular unit may include a self-contained bioreactor, the necessary liquid handling devices, refrigerators, tissue culture hoods and microbiology testing equipment, basic laboratory equipment (pipettors, sterile pipette tips, growth media, petri dishes, incubators and other general lab supplies), that has been tested and prevalidated to be compliant with the cGMPs or other regulatory body compliance requirements or in compliance with applicable codes, statutes, ordinances, regulations or equivalents. A modular unit for protein isolation, adjacent to but completely independent from the bioreactor unit, can be positioned and in communication with the bioreactor unit such that the materials manufactured in the bioreactor are rapidly and easily transferred to the protein isolation unit that has, pre-approved and validated protein separation units, e.g., centrifuges, liquid chromatography columns, spectrophotometers, polyacrylamide gel electrophoresis (PAGE) units and bulk packaging units. Next, the bulk protein may be transferred to a packaging unit that includes all the equipment necessary to fill individual doses of the protein, small molecule or other agent that is being manufactured.

Furthermore, the use of individual modules provides for the rapid exchange and continuous manufacture of product in case that one part of the manufacturing process must be changed or revalidated (e.g., in the case of the manufacture of a different biological or the detection of contamination) without the need to re-certify the entire facility. The addition of more modular units also allows for very rapid scale-up that can be customized for short periods of time. For example, a plant can receive the addition of modular units for scaling-up for a short period of time the manufacture and isolation of a vaccine for a short period of time and the redeployment of those units elsewhere upon completion of the production run. In fact, the present invention can be used in existing manufacturing facilities for short-term expansion of manufacturing capacity without the need for revalidation of the new manufacturing capacity or the expensive, long-term installation of an additional production line that will only be used for a short period of time.

The modular units of the present invention can be used as stand-alone facilities (provided they include within all the necessary equipment to manufacture, isolate and package) or may be placed within an existing structure. One example of such a structure is an empty factor or building. One such building could be of standard, pre-cast concrete construction, flat slab with flat, smooth floors, concrete tilt wall, double T precast ceiling and having steel or other walls (which can also be epoxy coated for cleanability). Within with building, the modular units provide the dedicated wet laboratory, growth, bioprocess and purification units necessary for manufacture. These units are simply lifted into position (e.g., pushed on air bearings, casters, pallets), connected to a power source and, if necessary, a water and/or a wastewater supply.

The present invention allows the designer to have the ability to connect one functioning modular unit to one or more additional functioning modules without disrupting the function or compliance of the original modular unit(s). Furthermore, the designer also has the ability to disconnect one functioning module from one or more additional functioning modules without disrupting the function or compliance of the original modular unit(s).

Yet another design option for the modular units of the present invention is the addition of an efficient energy recovery system that allows for energy recapture at a rate much higher than can be expected with existing methods. In this embodiment, the modular unit can also be connected to the central HVAC system of the building that houses the modular units. The intake 82 and exhaust 83 (see FIG. 5) of the redundant HVAC systems of the modular units can be connected to the central HVAC of the building thereby enhancing the energy efficiency of both units. For example, the modular units of the present invention can be placed inside of a second environment (a building with ambient temperature or less humidity), while having the modular unit interact dynamically with that second environment. In this manner of operation, the modular unit can use ambient air that does not need to be treated by a large and expensive external air handling unit.

Another vast improvement over existing designs is the ability of the modular units to service multiple clients with a single cluster of modular units. For example, a biotechnology research park or similar entrepreneurial facility could host various different companies, each having their own production facility or modular unit. One distinct advantage of using the modular units is that each completely self contained modular unit can contain an individual hazardous waste, spills, etc., without affecting any other structures (within a process flow or affecting an adjacent production facility, e.g., when a facility has various manufacturing lines or different companies).

When the modular unit needs to be connected to a source of water, the incoming water could be purified in an adjacent modular unit that could service various different production lines or the module itself could include a water purification unit. The modular unit of the present invention has the advantage that the redundant air handling units, electrical panels and even the water filtration units can be in the portion of the modular unit that is adjacent the clean room and can be serviced without service personnel having to enter the clean room area. When handling wastewater, the modular include can include sump pumps to eliminate waste. Furthermore, the bag in/bag out filters connected to the air handling units can also be changed without the need to enter the cleanroom area. These externally accessible portions of the buildings, or bays, allow for maintenance and maintenance personnel to service the unit without the need to gown-up and enter the clean room area.

Duplicate processes and equipment for air handling, exhaust, etc., with automatic fault tolerance/failover allows the user, e.g., from an external panel or via the internet, to switch-over from a first system to a second system if sensors within the modular unit sense a problem with a component in the first system or as part of regular maintenance.

Another feature of the modular units of the present invention is the ability to used connection devices that are well-known to maintenance personnel. For example, the modular units can use standard quick connectors for chilled water, electricity, etc. that allow the user to 'hot swap' the modular units externally. One advantage of the present invention is that it can take advantage of existing building infrastructure, e.g., mechanical equipment such as boilers, clean steam generator and compressors that can easily be connected to the units. The building's existing maintenance facilities and personnel serve to maintain services and cGMP equipment and environmental service compliance from outside the modular unit.

The present invention also includes a comprehensive management system that provides for the monitoring and maintenance of the module including electricity, water, fire, security, video, etc. externally.

The modular units of the present invention can be made from, for example, a welded aluminum frame, with an all aluminum wall structure of materials and coatings that are cleanable in the drug production environment and are compliant with the cGMP's as described by the USDA, CDC, FDA or equivalent regulatory agency. Stainless steel fixtures and surfaces may also be used when necessary, but could add more weight to the unit if a weight limit exists. The HVAC system can be divide the suite into four zones: a service hallway that will be a controlled non-classified space, gowning room and de-gowning rooms that will be classified at Class 10,000 (ISO 7) and a processing area that will can be classified at Class 10, 100, 1000, 10,000 or higher depending on the requirement. Within the modular unit, the appropriate pressure cascade of at least 0.035 inches of water column is created by adjusting the inlet and exhaust fan output and adjusting the return air volume in each space. For example, pressure changes are often made between the process area and gowning rooms, and gowning rooms to hallway. Exit air filtration will be provided by a "bag in/bag out" HEPA or ULPA filtration module. Incoming air will be pre-filtered with a series of pleated filters integral to the air handler, which can be changed externally from the clean room. Floors can be, e.g., monolithic epoxy, and ceilings can used non-shed 2×4 ceiling tiles along with the requisite fan powered HEPA filters.

Figure 5:
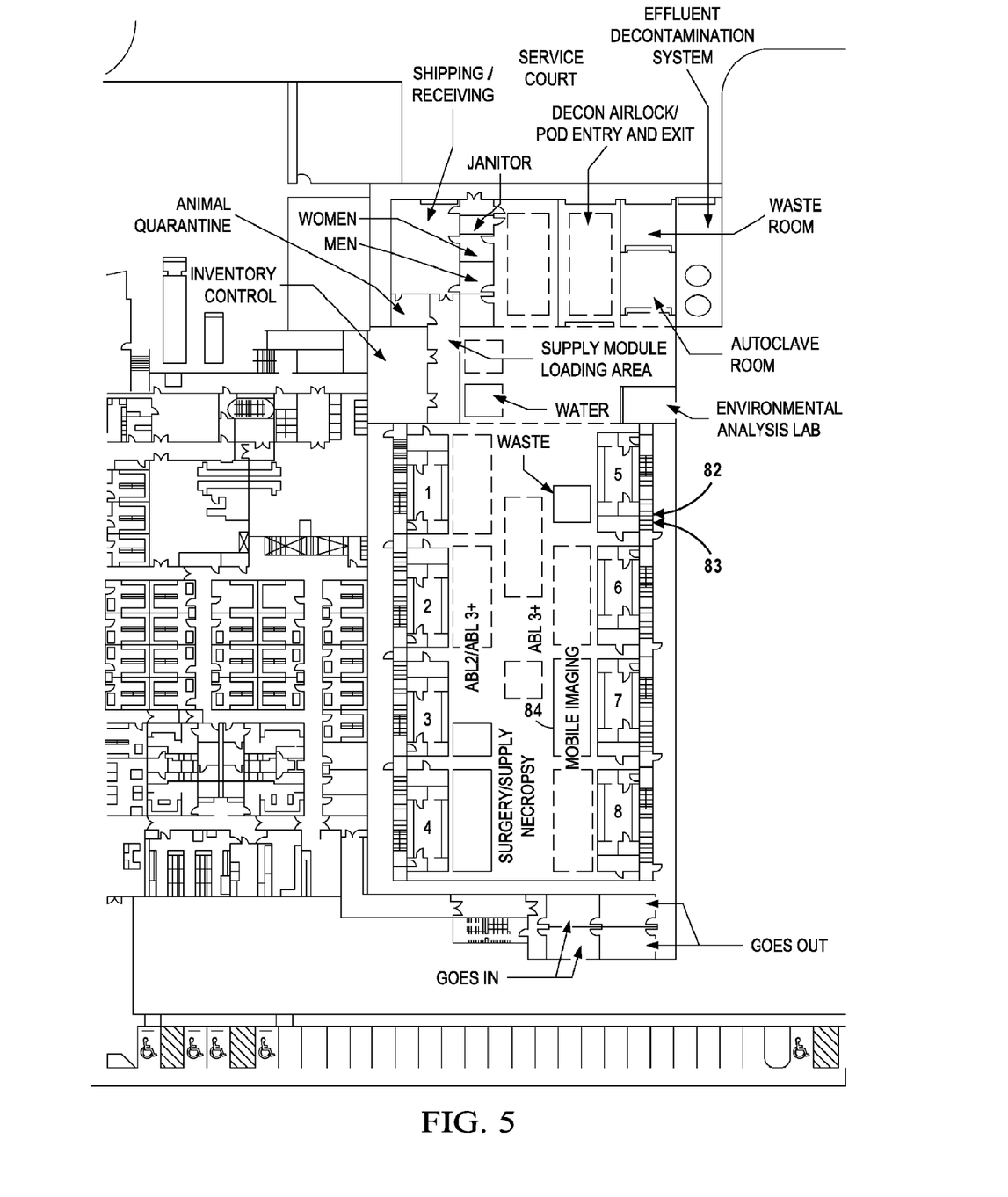
FIG. 5 is a top view of a cleanroom design for an Animal Biosafety Level 3 (ABSL3) facility.

The environment of the modular unit, e.g., within the clean room portion of the modular unit or even the maintenance portion of the modular unit, can be controlled and monitored externally using standard network information systems and remote systems monitoring computers 84 (see FIG. 5). All instrumentation and process equipment, where appropriate, will also have data interfaces 73 (see FIG. 1) installed on-site and remote data collection and will be internet protocol (IP) addressable.

The modular units will be equipped to easily interface with services such as a single electrical hook-up, chilled water supply, external gas supply, compressed air and liquid nitrogen if necessary to the process. Moreover, modular units can be outfitted with air bearings 79 (see FIG. 4), so that the modular units can be moved easily to other areas to be reconfigured in near real time to support necessary processes and surge capabilities without disturbing ongoing operations.

Each modular unit can be preassembled with a final documentation package that can include: the design, structural, mechanical, electrical and plumbing drawings, system dossiers, installation qualification and operational qualification plan and executed documents, maintenance logs, and pro-forma quality assurance documents including basic standard operating procedures. These may be provided in hard copy, or provided via a display panel within the modular unit or externally (including within the maintenance bay) that is electronic and can include the necessary passcode/password protection. In fact, the entire unit can include safety features such as passcode/password protection to enter the clean room and/or the maintenance bay, the systems within the clean room (e.g., all the equipment within the room, e.g., bioreactors, columns, centrifuges, computers, assembly lines, input/output lines (liquid, solid, gas), electronic connections (including hard-wire and wireless connections), data storage, liquid and sample storage, storage of controlled substances (including safes or storage cages), incubators, refrigerators or freezers, −70° or other low temperature storage and entry or access to laboratory equipment and supplies.

GENERAL: The redundant HVAC system can include two or more 100% redundant air systems, each having an air handler with discharge air damper, exhaust fan with discharge air damper, and/or an electric duct heater. In operation, the HVAC system can include: a Building Automation System (BAS) 72 (see FIG. 1) that can start/stop the HVAC (and other) equipment electronically or mechanically. An air system that can be "ON" continuously (e.g., have instantaneous fail-over between systems, including a continuously operating "unoccupied" mode). A Lead and Lag systems can be rotated based on need, e.g., weekly or monthly. The air system can include one or more dampers, end switch closes; lag system exhaust fan discharge and air damper controllers; fan discharge switches; valve control and even duct heater controls.

SUPPLY FAN CONTROL: The constant speed supply fans can be operated from within the clean room, remote automatic start/stop switches, and/or a Building Automation System (BAS) to monitor, e.g., fan status. If the Lead supply fan stops for any reason, the Lead air system will be stopped per the air system stop command and, optionally, an auditory, visual, and/or silent alarm.

TEMPERATURE CONTROL: Temperature in the unit can be controlled via the air handling unit and/or a chilled-water (CHW) valve that modulates to control coil leaving air temperature and/or control of the temperature in the clean room, gown or de-gowning room and/or the maintenance room. The system may also include a duct heater that can modulate to control space temperature.

EXHAUST FAN CONTROL: The constant speed exhaust fans will be capable of remote automatic start/stop and can be monitored via the BAS, which monitors fan status. If the fan(s) stop for any reason, the air handling system will be stopped, and an alarm will be sent to the BAS and the redundant unit will immediate begin operating.

CHILLED WATER SYSTEM CONTROL: The chilled water system will be capable of remote automatic start/stop. The chilled water system will be enabled whenever the air-handling unit (AHU) entering air temperature is above the chilled water coil discharge air setpoint temperature. On a system start command, the CHW pump will start and the chiller controls will be enabled; the chiller will start when flow is proved. On a system stop command, the chiller will be disabled, and the pump will continue to run for five minutes and then be stopped. The BAS will monitor pump status. If the pump fails, the chiller will be disabled, and an alarm will be sent to the BAS. The BAS will monitor chiller status and can provide instantaneous fail-over capability by automatically switching to a redundant chiller. If the chiller fails, the pump will be stopped five minutes later, and an alarm will be sent by the BAS.

ADDITIONAL MONITORING POINTS AND SYSTEM ALARMS: Space pressure can be monitored, e.g., the pressure in the cleanroom. If the pressure drops to 0.0" water column (WC) or below, an alarm can be sent to the BAS. A variety of pressure sensors mounted in the modular unit (e.g., one in the corridor, one each in both the gowning rooms and one in the main lab area of the modular unit) can be provided and monitored. When an alarm is sent to the BAS, the system can call pre-programmed emergency telephone numbers and/or communication electronically via text or email.

Additional Points that can be monitored in the modular unit include, e.g., a static pressure blowout sensor in communication with the air handling units (AHU's) For example, the BAS can determine if there is a belt failure in either of the AHU's or EF's by using, e.g., an amp sensor that monitors the change in amp draw on the motor. Another sensor can be a pitot tube in the supply air duct and exhaust air duct that monitors static pressure connected to the BAS. Also, gravity dampers, automatic dampers and damper end switches and the controls can also be connected to and monitored by the BAS.

Figure 1:
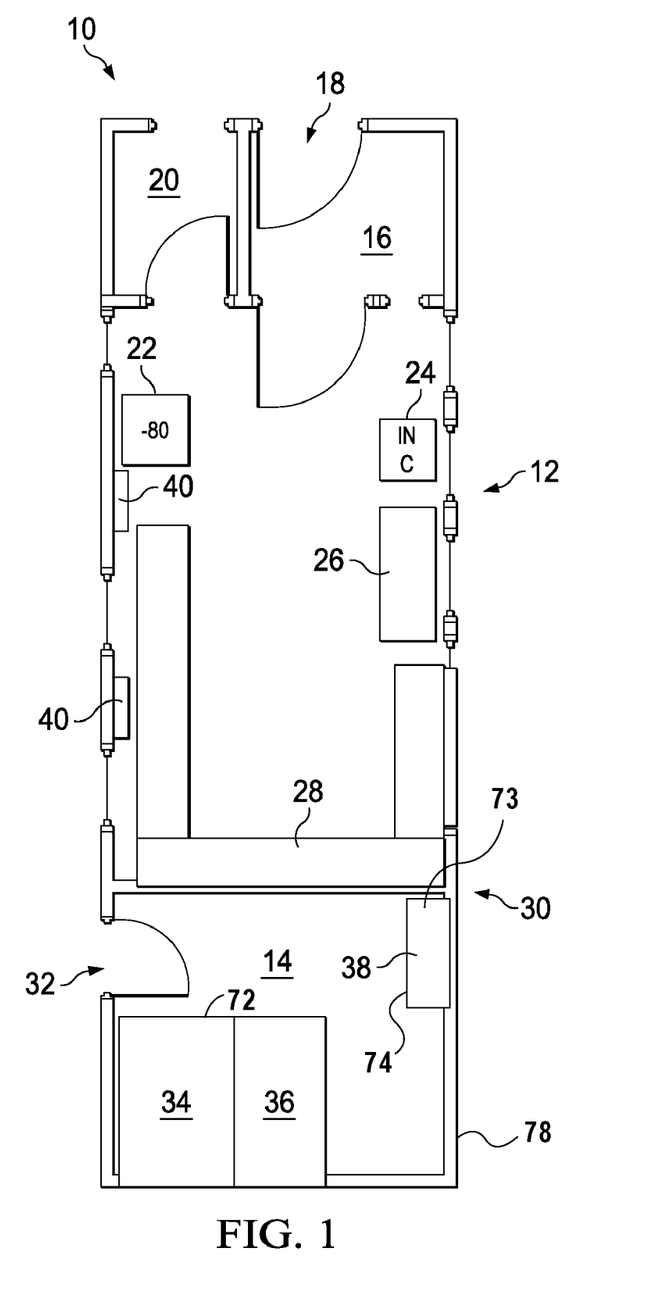
FIG. 1 is a top view of a modular unit of the present invention.

FIG. 1 shows a modular unit 10 of the present invention. The modular units of the present invention can be made from, for example, a welded aluminum frame 78, with an all aluminum wall structure of materials and coatings that are cleanable in the drug production environment and are compliant with the cGMP's as described by the USDA, CDC, FDA or equivalent regulatory agency. The modular unit 10 includes two parts, a clean room 12 and a maintenance room 14. The clean room 12 includes a gowning room 16, which provides in this example the sole entry point 18 to the clean room 12, and a de-gowning room 20. In this configuration, the clean room 12 includes a −80° C. freezer 22, an incubator 24, a biosafety cabinet 26 and cabinetry 28, which is pre-installed in this configuration of the clean room 12. The −80° C. freezer 22, an incubator 24, a biosafety cabinet 26 and cabinetry 28 can be attached to the walls and floor by pre-installed attachment points that may be positioned throughout the interior of the clean room 12, or may be custom installed. The maintenance room 14 is separated from the clean room 12 by a wall 30 that isolates the clean room 12 from the maintenance room 14. The maintenance room 14 has a single point of entry 32, through which maintenance personnel can attend to the physical plant portions of the modular unit 10 without needing to access the clean room 12. All the wiring 75 (see FIG. 3), plumbing and air conduits 60 and 76 (see FIG. 3) of the modular unit (not depicted), are pre-installed in the walls of the modular unit and sealed such that the clean room 12 is isolated from the environment surrounding the clean room 12. A redundant HVAC system 34 is found in the maintenance room 14 and can include a bag-in/bag-out filtration system 36. Electrical box 38 is found within the maintenance room 14 and can include not only an electrical panel/breaker box 74 for the modular unit 10, but may also include wired and/or wireless communications equipment 73. In this example, the return air ducts 40 are positioned in the floor of the clean room and return via a sealed duct to the HVAC system 34.

Figure 2:
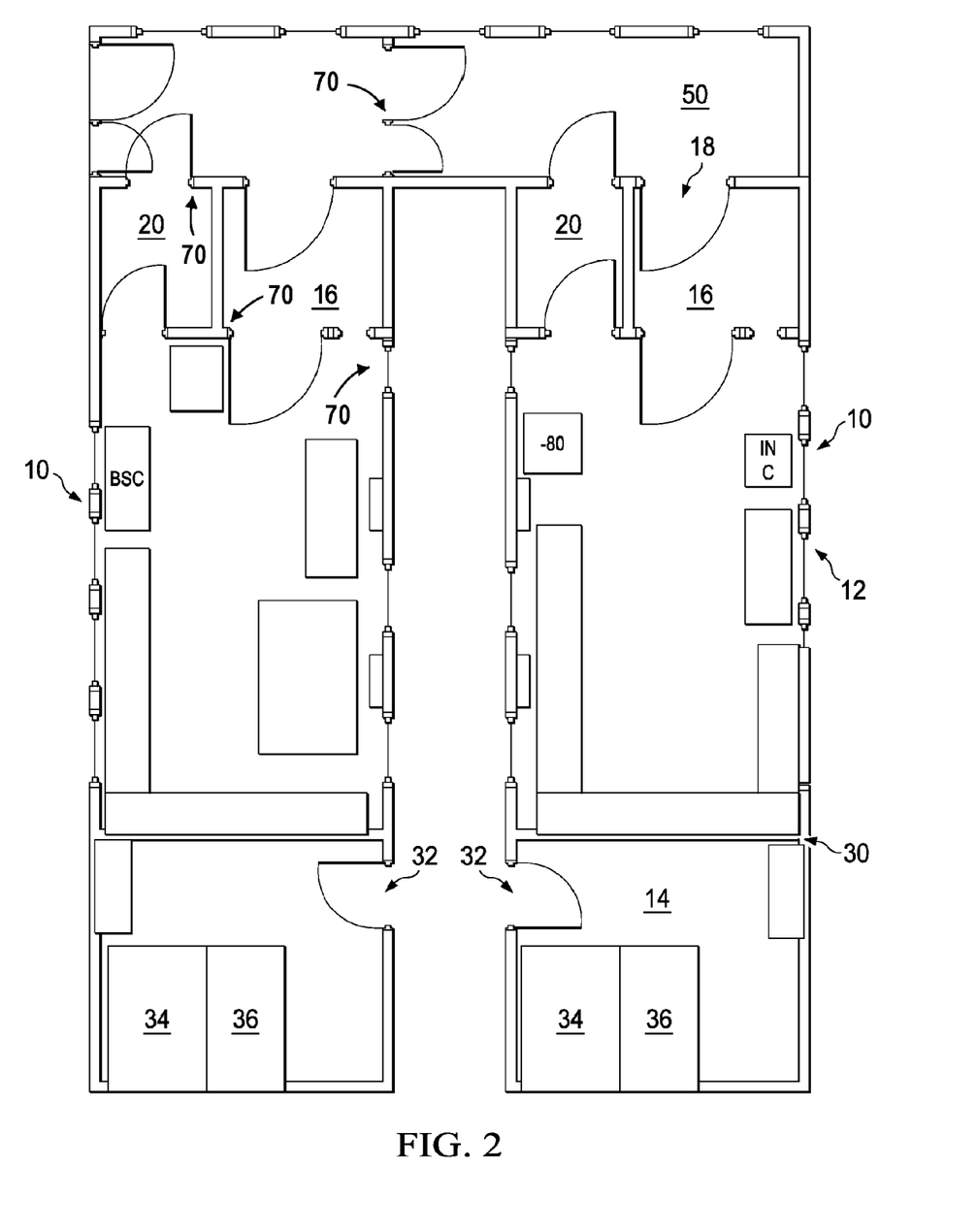
FIG. 2 is a top view of a pair of modular units of the present invention.

In the configuration depicted in FIG. 2, two modular units 10 are shown and can be connected via a service hallway 50, which can be a controlled space, gowning room and de-gowning rooms that will be classified at Class 10,000 (ISO 7) and a processing area that will can be classified at Class 10, 100, 1000, 10,000 or higher depending on the requirement.

Figure 3:
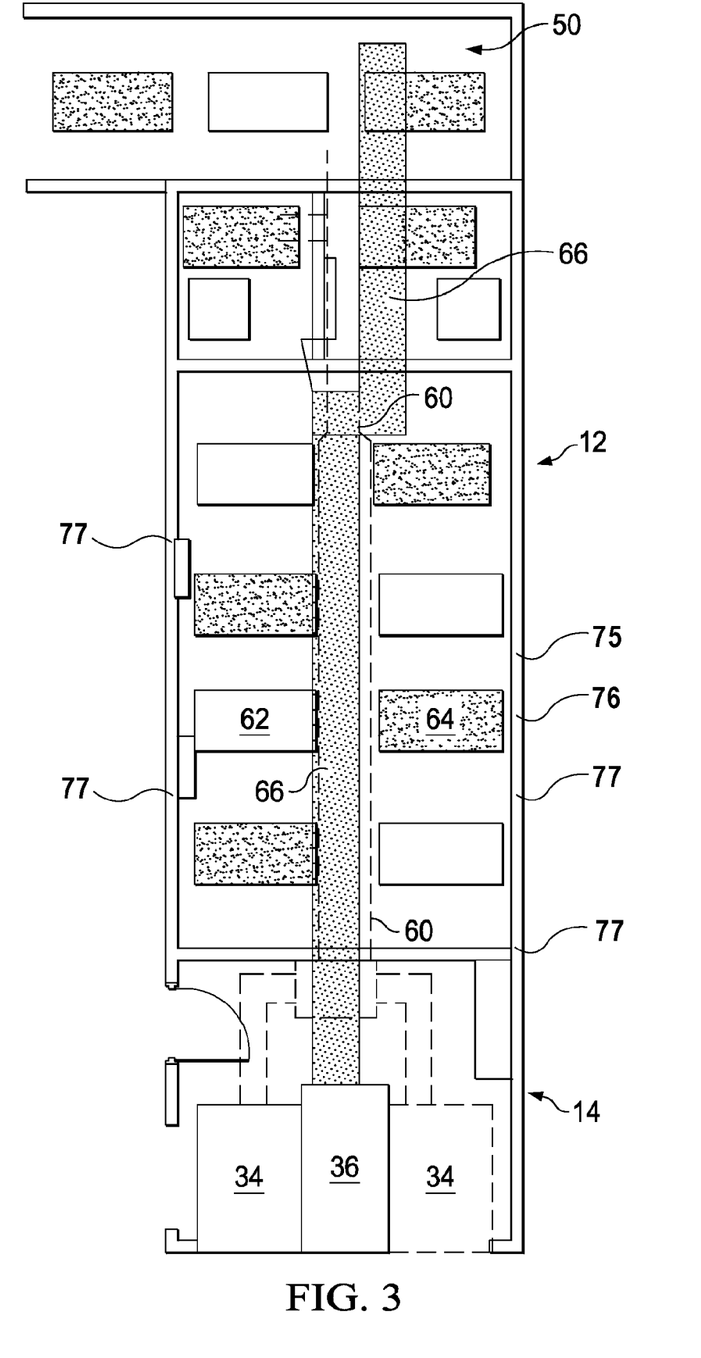
FIG. 3 is a top view of another pair of modular units of the present invention.
Figure 4:
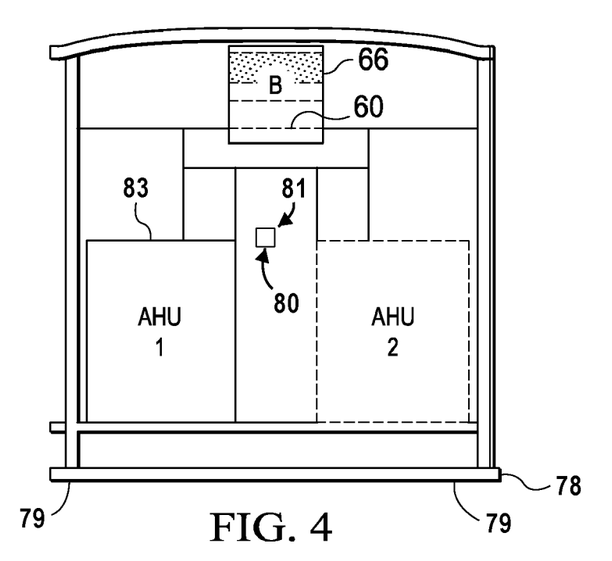
FIG. 4 is a side view of a modular unit of the present invention.

FIG. 3 shows two modular units 10, with a service hallway 50 and the details of an air conduit and filtration system connected to the air handling units 60. Within the modular unit 10, the appropriate pressure cascade of at least 0.035 inches of water column is created within the conduits 60 by the use of changes in conduit size and/or baffles and return ducts 66. For example, pressure changes are often made between the process area and gowning room 16, and de-gowning room 20 to hallway 50. Exit filtration will be provided by a "bag in/bag out" HEPA or ULPA filtration 36, and HEPA filters 62, which alternate with lighting fixtures 64. Incoming air may be pre-filtered with a series of pleated filters integral to the air handler system 24, which can be changed externally from the clean room 12. Floors can be, e.g., monolithic epoxy, and ceilings can used non-shed 2×4 ceiling tiles along with the requisite fan powered HEPA filters. FIG. 4 shows a side view in which the conduits 60 are shown in relation to return ducts 66.

The present invention includes one or more of the following sensors and, optionally, electronic reporting units that report, in real-time or based on a pre-determined or programmable schedule, wherein the sensors can report on the status of the various areas or systems of the modular units, including: Room temperature (degrees C. or F); Room relative humidity; Four Pressure sensors 70 (see FIG. 2) (e.g., 1 in the corridor, 1 in gown-in area, 1 in gown-out area, 1 in lab/cleanroom); Ambient air temperature (degrees C. or F); Ambient relative humidity; HEPA filter lifecycle status (e.g., measured in inches e.g.); Chilled water temperature (degrees C. or F); Chilled water pressure (psi); Supply fan status (2 each); Exhaust fan status (2 each); Chilled water status (degrees C. or F); Chilled water supply and return temperature (degrees C. or F); Chilled water pump status or various sensors to read status and performance on: temperature, CO2, airflow, off/on, security, door position, personnel entry and exit, inventory control.

Hardened for harsh environments: The structure and portability of the cleanrooms provide for use as a facility hardened for harsh environments. As described previously herein the cleanroom can be used as a stand-alone unit or can be combined with other modules that may serve as support units, such as a unit to contain chiller equipment, and/or a unit to contain mechanical equipment (such as a generator set, a compressor, and/or water containment and or purification equipment). Such a cleanroom or set of cleanrooms can be shipped into an area via various means, such as C17 airforce transport, truck, or boat with the intent of quick set up of a cleanroom facility in an area that has no infrastructure for such. A set-up like this could also be quickly dismantled and removed.

Hospital/Surgical/Triage: The structure, portability, and controlled environment of the cleanrooms provides for use as a hospital unit or units, surgical suite or suites, and/or triage facilities for areas in which there is otherwise no available infrastructure for such facilities or in areas in which such facilities have been recently destroyed, or in areas in which additional facilities are required before one can be constructed. The controllability of the interior environment and ability to create a Class 100 or Class 1000 compliant environment would be suitable for a burn unit, where patients are at particular risk for infection from exposure to airborne microbes.

Massively portable: The units described herein are compact enough to be transported via various modes, including but not limited to road, train, sea, and air. Units may be placed on a flatbed trailer pulled by a semi, sealed in shipping containers for rail or sea transport, or placed upon an air carrier, such as a Boeing C-17 Globemaster III military transport plane. Units are designed and engineered to withstand the physical stress of travel via road, train, sea, and air and are of a weight such as to be portable via these transportation means. The units of the present invention can also be built with structural lifting points and lifted via hydraulic lifts inserted into these points to be raised to slightly above the level of a flat-bed trailer. The flat-bed trailer is then backed under the unit and lowered and secured for transport.

Designed for maximal cleanability: As cleanability is crucial for the aseptic environment provided by the cleanrooms, floors, windows, and walls are made in such a way as to reduce, if not completely eliminate, cracks, crevices, joint spaces and other areas in which dust and microbes may rest or accumulate. Windows are flush-mounted to the interior to reduce small areas in which dust and microbes may accumulate and to increase to ease of cleaning of the joint at which a window meets a wall. Floors are covered with a monolithic application of an epoxy resin. Walls are likewise covered with a monolithic application of an epoxy resin. This creates increased cleanability of both wall and floor surfaces, but more importantly, reduces joint and cracks within both the wall and floor surfaces themselves, as well as eliminating a joint and or crack where wall meets floor.

Cleanrooms are constructed in multiple dimensions, including 12 feet by 43 feet, 15 feet by 43 feet, and 18 feet by 43 feet. Height may be from 10 feet to 18 feet. Lengths may be adjusted as required below 43 feet. These dimensions allow for ultimate flexibility in both use and transport. 12-foot-wide units are most applicable for air and sea transport, while road transport allows for up to 18 feet in width. Height may be increased to 18 feet to allow for the installation of larger equipment, such as large bioreactors that require such headroom.

The cleanrooms of the present invention can be made with monolithic epoxy walls and floors. This provides a very rugged surface and highly cleanable surface for use in Biological Safety Level 3 (BSL3) and Animal Biosafety Level 3 (ABSL3). The clean rooms can be operated in a negative pressure totally isolated mode and when connected to a modular clean hallway. This fact provides at least 3 levels of air cascade essential in BSL3 applications. A new approach has also been designed by the present inventors for an ABSL3 facility that uses the portability of the clean rooms to maximum advantage and a new paradigm. The design is depicted in FIG. 5. The concept is that the animals stay in one place and that services and procedures are brought to them by movable clean rooms. The outer row of cleanrooms represents areas for animals being treated in separate studies.

Services like food supply and waste removal can be facilitated by movable clean rooms. Experimental support services like imaging, surgery, necropsy and others can be brought to the individual experimental animal containment area. The animals can be transferred in containment to the service required and returned if applicable to their habitat clean rooms. This approach allows superior containment for these processes since the animals will not be transported throughout a building to different laboratories for treatment or sophisticated diagnostic and other procedures. Containment is facilitated by a docking system that provides a contained pass through for animals. The pressure can be maintained negatively for both cleanrooms in relation to the gray space. Both clean rooms are isolated from the gray space by filtration on both inlet and exhaust air.

The clean rooms can be used as manufacturing or medical facilities for the military and others by being constructed for air transports on cargo planes such as the C-17 military transport. Factories configured by multiple modules can be transported and enable quickly with self-contained power, steam and chilled water service modules. Other anticipated uses are for medical and surgical treatment suites in remote areas.

Filling of antigens at the site of a bioterrorism or biological "hot zone": A mobile clean room can be designed with a sterile filling machine to fill injector tips that are used for air powered injection. This indicates that a clean room could be airlifted to a site of an event and that bulk pharmaceutical substance could be delivered directly from the manufacturer to the site in bulk fill containers containing hundreds of thousands of doses, e.g. 250 ml and 1 mg per ml per ml would yield 2500 doses at 100 micrograms per dose at a dose size of 0.1 ml. The fact that the bulk material could be delivered to the site with no need to fill into individual doses. This could save weeks in the delivery to a "hot zone" since an intermediate fill step would not have to be done.

A specially designed chamber will allow the transfer of waste from the clean room to a sealed portable container for transport of solid and liquid wastes from a process. This container is portable and docks with a dedicated pass through to transfer waste materials. The outer door of the pass through is then closed followed by the inner door on the clean room and the transfer is complete.

Figure 6:
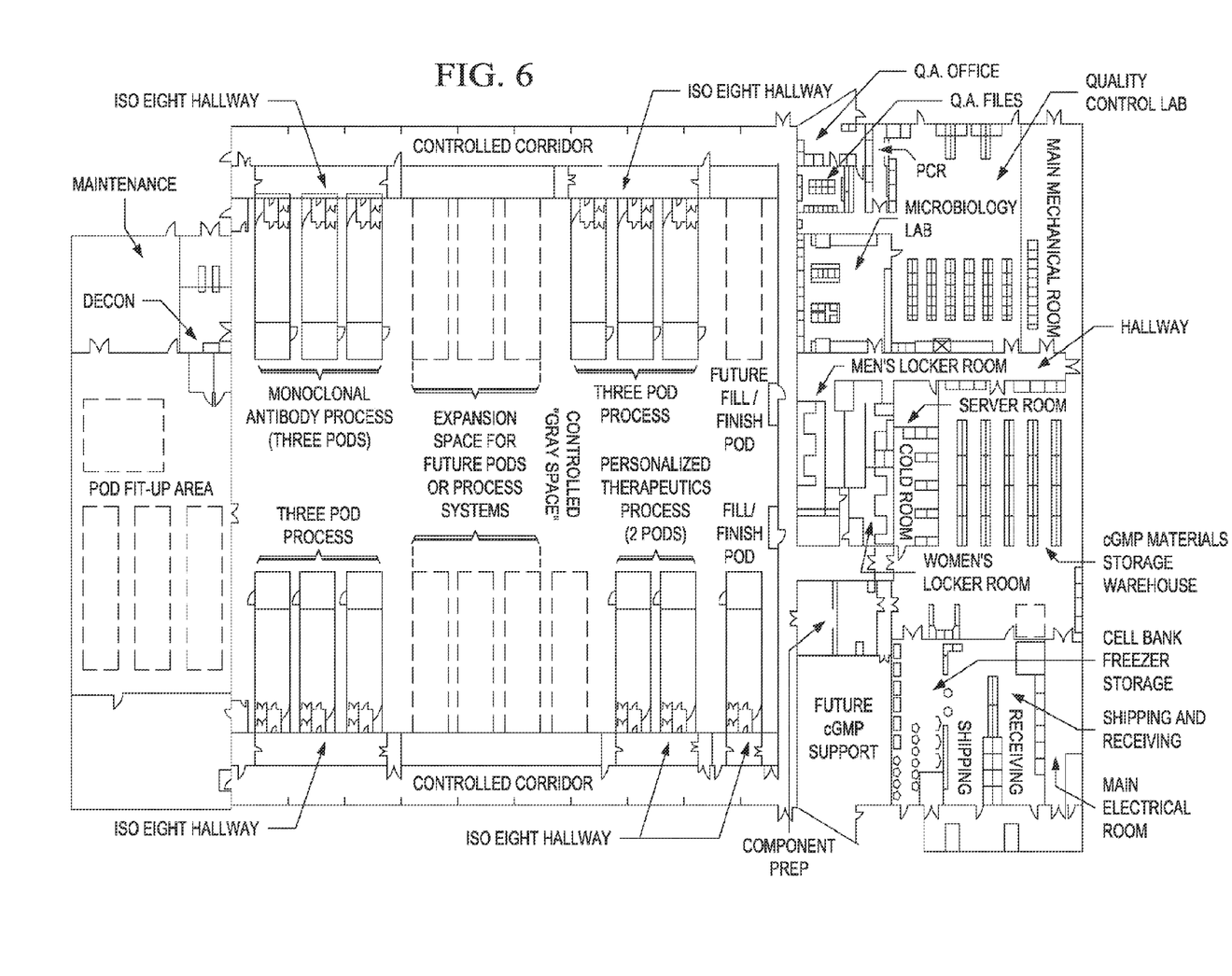
FIG. 6 is a top view of a cleanroom concept for use in a multiple biotherapeutics manufacturing process.
Figure 7:
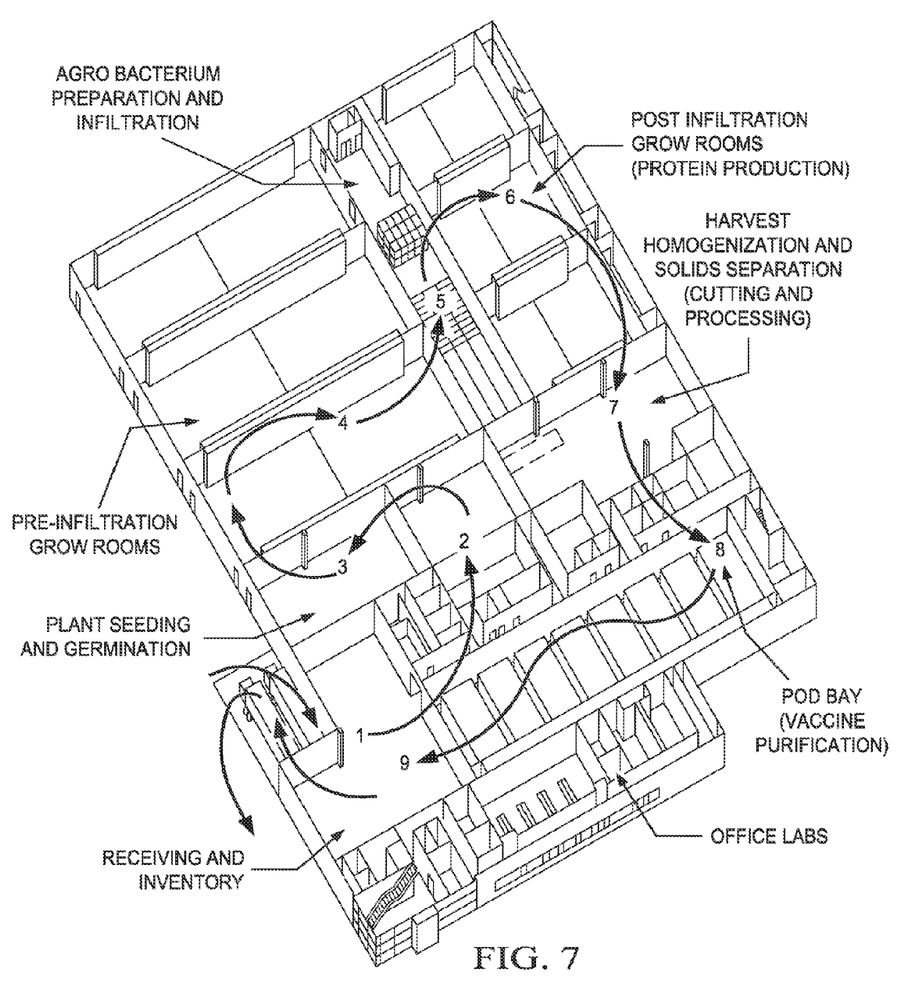
FIG. 7 is a top view of a combination processing facility that include one or more of the modular units of the present invention that includes various components in working communication.

The clean rooms of the present invention have been included in a new concept involving up to six different biotherapeutics manufacturing process can be done in the same gray space infrastructure as depicted in FIG. 6. Because of the containment and flexibility multiple processes can be implemented and changed without disturbing other stakeholders in the space.

Modular clean rooms are being used for the downstream portion processing in a biologics or a very large commercial vaccine facility. Eight clean rooms were used for downstream processing including tangential flow filtration, chromatography, sterile filling, buffer preparation, equipment washing and quality control testing.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A manufacturing system comprising: a building shell; at least one elongate corridor extending within the building shell;
   a supply of two or more utilities from the building shell, wherein at least two of the two or more utilities are selected from the group consisting of (a) clean air, (b) chilled water, (c) electricity, and (d) nitrogen;
   a rectangular first movable manufacturing bay disposed within the building shell and positioned with a short end up against the corridor and removably coupled for receiving the utilities;
   a first clean room defined by the first movable manufacturing bay and accommodating a first facility for performing at least a part of a manufacturing process;
   a first mechanical room within an end of the first movable manufacturing bay distal the corridor, the first mechanical room supplying one or more first utilities to the first clean room;
   a rectangular second movable manufacturing bay disposed within the building shell and positioned with a short end up against the corridor and removably coupled for receiving the utilities;
   a second clean room defined by the second movable manufacturing bay and accommodating a second facility for performing at least a part of a manufacturing process;
   a second mechanical room within an end of the second movable manufacturing bay distal the corridor, the second mechanical room supplying one or more second utilities to the second clean room;
   a first entry point disposed between the first clean room and the corridor when the first movable manufacturing bay is removably coupled to the corridor, the first entry point for controlling access to and from the first clean room;
a second entry point disposed between the second clean room and the corridor when the second movable manufacturing bay is removably coupled to the corridor, the second entry point for controlling access to and from the second clean room;
wherein the first and second entry points are connected by the corridor such that personnel can pass between the first and second clean connect areas via the corridor;
wherein each of the first and second entry points comprises a gowning room and a de-gowning room separated from each other by a partition, wherein operating personnel can gown and de-gown within the gowning and de-gowning rooms, respectively;
wherein the first and second mechanical rooms each have an entrance for personnel from outside the first and second manufacturing bays that is separate from the first and second entry point and configured to be serviced without entering the first or second clean rooms or the corridor; and
wherein an exhaust connection from the first movable manufacturing bay is coupled to a central HVAC system of the building shell.

2. The system of claim 1, wherein the first and second utilities are selected from the group consisting of (a) clean air, (b) chilled water, (c) electricity, and (d) nitrogen.

3. The system of claim 2, further comprising a duplicate utility supply system disposed in the first mechanical room or the second utility room, the duplicate utility supply system for providing utilities to the first and second clean rooms in case of a failure.

4. The system of claim 1, wherein the first and second entry points are within the first and second movable manufacturing bays, respectively.

5. The system of claim 1, wherein the rectangular second movable manufacturing bay is disposed parallel to the first movable manufacturing bay.

6. A manufacturing system comprising: a building shell; at least one elongate corridor extending within the building shell;
a supply of two or more utilities from the building shell, wherein at least two of the two or more utilities are selected from the group consisting of (a) clean air, (b) chilled water, (c) electricity, and (d) nitrogen;
a rectangular first movable manufacturing bay disposed within the building shell and positioned with a short end up against the corridor and removably coupled for receiving the utilities;
a first clean room defined by the first movable manufacturing bay and accommodating a first facility for performing at least a part of a manufacturing process;
a first mechanical room within an end of the first movable manufacturing bay distal the corridor, the first mechanical room supplying one or more first utilities to the first clean room;
a rectangular second movable manufacturing bay disposed within the building shell and positioned with a short end up against the corridor and removably coupled for receiving the utilities;
a second clean room defined by the second movable manufacturing bay and accommodating a second facility for performing at least a part of a manufacturing process;
a second mechanical room within an end of the second movable manufacturing bay distal the corridor, the second mechanical room supplying one or more second utilities to the second clean room;
a first entry point disposed between the first clean room and the corridor when the first movable manufacturing bay is removably coupled to the corridor, the first entry point for controlling access to and from the first clean room;
a second entry point disposed between the second clean room and the corridor when the second movable manufacturing bay is removably coupled to the corridor, the second entry point for controlling access to and from the second clean room;
wherein the first and second entry points are connected by the corridor such that personnel can pass between the first and second clean connect areas via the corridor;
wherein each of the first and second entry points comprises a gowning room and a de-gowning room separated from each other by a partition, wherein operating personnel can gown and de-gown within the gowning and de-gowning rooms, respectively;
wherein the first and second mechanical rooms each have an entrance for personnel from outside the first and second manufacturing bays that is separate from the first and second entry point and configured to be serviced without entering the first or second clean rooms or the corridor; and
wherein each of the first and second manufacturing bays includes a welded aluminum frame structure and air-bearings.

7. The system of claim 6 wherein the first manufacturing bay resides on flat, smooth floors within the shell building, wherein the air bearings permit movement of the first and second manufacturing bays.

8. The system of claim 6, wherein the first and second utilities are selected from the group consisting of (a) clean air, (b) chilled water, (c) electricity, and (d) nitrogen.

9. The system of claim 8, further comprising a duplicate utility supply system disposed in the first mechanical room or the second utility room, the duplicate utility supply system for providing utilities to the first and second clean rooms in case of a failure.

10. A cleanroom system comprising:
a building shell;
an elongate service hallway;
a rectangular first modular unit within the building shell and connected at a short end with the service hallway, the first modular unit comprising:
a first controlled air, sealable, sterilizable clean room within the first modular unit, the first clean room having an entry point for personnel from the service hallway;
a first HVAC system within a first mechanical room of the first modular unit, the first HVAC system connected with the first clean room via a supply air duct and a return air duct, wherein the first modular unit is connected to the building shell for electricity and water, wherein the first mechanical room has an entrance at a distal end of the first modular unit to the service hallway; and
a pressure sensor within the first clean room, the pressure sensor connected to a building automation system (BAS) within the first modular unit, wherein the BAS is configured to transmit an alarm through a wired or wireless data interface to a computer outside the first modular unit and within the building shell; and a rectangular second modular unit within the building shell and connected at a short end with the service hallway, the second modular unit comprising:
  a second controlled air, sealable, sterilizable clean room within the second modular unit, the second clean room having an entry point for personnel from the service hallway; and
  a second HVAC system within a second mechanical room of the second modular unit, the second HVAC system connected with the second clean room via a supply air duct and a return air duct, wherein the second modular unit is connected to the building shell for electricity and water, wherein the second mechanical room has an entrance at a distal end of the second modular unit to the service hallway.

11. The system of claim 10 wherein each of the first and second modular units comprise a welded aluminum frame structure and air-bearings.

12. The system of claim 10 wherein the first modular unit further comprises:
  a welded aluminum frame forming a structure of the first modular unit; and
  air-bearings under the structure.

13. The system of claim 12 wherein the first modular unit resides on flat, smooth floors within the shell building, wherein the air bearings permit movement of the first modular unit.

14. The system of claim 13 wherein the first modular unit further comprises:
  a flexible connector for connecting to the unit a boiler or clean steam generator from the shell building, the flexible connector allowing the first modular unit to be moved without disconnecting from the boiler or clean steam generator.

15. The system of claim 10 further comprising:
  universal flexible connectors for connecting the first modular unit to electrical, water, drain water, wastewater, gas, chilled water, and hot water inputs or outputs of the building shell.

16. The system of claim 10, wherein the rectangular second modular unit is disposed parallel to the first modular unit.

17. A set of rectangular, self-contained, biosafety unitary modular units comprising:

at least one controlled air, sealable, sterilizable clean room within each modular unit, the clean room having an entry point at a short end of the modular unit for personnel;
a mechanical system room within each modular unit and at a distal end of the modular unit from the clean room entry point, the mechanical system room having an entrance that is separate from the clean room entry point, wherein the mechanical system room is configured to be serviced without entering the clean room;
an HVAC system within each modular unit, the HVAC system connected with the modular unit's clean room via a supply air duct and a return air duct, the HVAC system configured to draw air from an ambient environment outside of the modular unit;
a pressure sensor within each clean room, the pressure sensor connected to a building automation system (BAS) within the respective modular unit, wherein the BAS is configured to automatically transmit an alarm through a wired or wireless data interface to outside the modular unit; and
an electrical panel within each mechanical system room, the electrical panel accessing a power wiring that is connected via sealed conduits to outlets within the respective clean room;
an elongate service hallway, each rectangular modular unit connected at the short end with the service hallway, each mechanical system room entrance distal to the service hallway; and
a building shell enclosing the modular units and service hallway.

18. The set of modular units of claim 17, further comprising:
  a welded aluminum frame forming a structure of each modular unit, thereby being lighter weight than steel; and
  air-bearings under each structure.

19. The set of modular units of claim 17 further comprising:
  an exhaust connection from each modular unit with a central HVAC system of the building shell.

20. The set of modular units of claim 17, wherein the modular units are disposed parallel to each other.

* * * * *